United States Patent
Adams et al.

(10) Patent No.: US 10,973,618 B2
(45) Date of Patent: Apr. 13, 2021

(54) EMBOLIC PROTECTION DEVICE (71) Applicant: AGA Medical Corporation, Plymouth, MN (US)

(72) Inventors: Daniel Adams, Long Lake, MN (US); Sara Jane Gries, Plymouth, MN (US); Cheryl A. Lecy, Stacy, MN (US); Brooke Ren, Maple Grove, MN (US); Mathias Charles Glimsdale, St. Michael, MN (US); Carolyn Cochenour, Minneapolis, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 1167 days.

(21) Appl. No.: 13/782,703

(22) Filed: Mar. 1, 2013

(65) Prior Publication Data
US 2014/0249567 A1 Sep. 4, 2014

(51) Int. Cl.
A61F 2/01 (2006.01)

(52) U.S. Cl.
CPC ............... *A61F 2/01* (2013.01); *A61F 2/013* (2013.01); *A61F 2/011* (2020.05); *A61F 2002/016* (2013.01)

(58) Field of Classification Search
CPC .. A61F 2/856; A61F 2/01; A61F 2/013; A61F 2002/011; A61F 2002/016; A61F 2/011
See application file for complete search history.

(56) References Cited

U.S. PATENT DOCUMENTS

| 5,279,573 | A | * | 1/1994 | Klosterman | A61M 25/09041 206/403 |
|---|---|---|---|---|---|
| 5,527,337 | A | | 6/1996 | Stack et al. | |
| 5,800,457 | A | | 9/1998 | Gelbfish | |
| 5,800,525 | A | * | 9/1998 | Bachinski | A61F 2/01 606/200 |
| 5,906,641 | A | | 5/1999 | Thompson et al. | |
| 6,361,545 | B1 | | 3/2002 | Macoviak et al. | |
| 6,540,767 | B1 | | 4/2003 | Walak et al. | |

(Continued)

FOREIGN PATENT DOCUMENTS

| WO | 0053119 A1 | 9/2000 |
|---|---|---|
| WO | 2006131930 A2 | 12/2006 |

(Continued)

OTHER PUBLICATIONS

International Search Report for Application No. PCT/US2013/078301 dated Mar. 28, 2014.

(Continued)

*Primary Examiner* — Tan-Uyen T Ho
*Assistant Examiner* — Rachel S Highland
(74) *Attorney, Agent, or Firm* — Lerner, David, Littenberg, Krumholz & Mentlik, LLP (57) ABSTRACT

Embolic protection devices and systems capture and/or deflect emboli from entering one or more arterial branches of the aorta. An embolic protection device may include an anchor section that is positionable within an arterial branch of the aorta and a shield section that is operatively coupled to the anchor section. The shield section is positionable relative to one or more ostia of the aortic branches and is held in that position by the anchor section.

21 Claims, 8 Drawing Sheets

(56) References Cited

U.S. PATENT DOCUMENTS

| | | | |
|---|---|---|---|
| 6,558,405 B1* | 5/2003 | McInnes | A61F 2/013 606/200 |
| 9,480,548 B2 | 11/2016 | Carpenter | |
| 2001/0044634 A1 | 11/2001 | Don Michael et al. | |
| 2003/0004539 A1 | 1/2003 | Linder et al. | |
| 2004/0153118 A1* | 8/2004 | Clubb | A61F 2/013 606/200 |
| 2004/0215167 A1* | 10/2004 | Belson | A61F 2/01 604/526 |
| 2005/0143817 A1* | 6/2005 | Hunter | A61B 17/11 623/11.11 |
| 2006/0100662 A1 | 5/2006 | Daniel et al. | |
| 2006/0161241 A1* | 7/2006 | Barbut | A61F 2/013 623/1.15 |
| 2006/0229658 A1* | 10/2006 | Stivland | A61F 2/013 606/200 |
| 2006/0271098 A1* | 11/2006 | Peacock, III | A61F 2/013 606/200 |
| 2006/0293706 A1 | 12/2006 | Shimon | |
| 2007/0088387 A1* | 4/2007 | Eskridge | A61B 17/12022 606/213 |
| 2007/0203559 A1* | 8/2007 | Freudenthal | A61B 17/22 623/1.3 |
| 2007/0270901 A1* | 11/2007 | Shimon | A61F 2/01 606/200 |
| 2008/0119886 A1* | 5/2008 | Greenhalgh | A61B 17/0057 606/200 |
| 2008/0140110 A1* | 6/2008 | Spence | A61F 2/06 606/200 |
| 2008/0255603 A1* | 10/2008 | Naor | A61F 2/00 606/200 |
| 2008/0262518 A1* | 10/2008 | Freudenthal | A61B 17/0057 606/151 |
| 2009/0099647 A1* | 4/2009 | Glimsdale | A61B 17/0057 623/1.35 |
| 2009/0187210 A1 | 7/2009 | Mackiewicz | |
| 2009/0254172 A1* | 10/2009 | Grewe | A61F 2/86 623/1.15 |
| 2009/0326575 A1* | 12/2009 | Galdonik | A61F 2/01 606/200 |
| 2010/0312268 A1 | 12/2010 | Belson | |
| 2010/0324589 A1* | 12/2010 | Carpenter | A61B 17/12022 606/200 |
| 2011/0022076 A1* | 1/2011 | Lashinski | A61F 2/013 606/200 |
| 2011/0190863 A1 | 8/2011 | Ostroot et al. | |
| 2011/0282379 A1* | 11/2011 | Lee | A61F 2/01 606/200 |
| 2012/0172920 A1 | 7/2012 | Fifer et al. | |
| 2012/0179033 A1 | 7/2012 | Merhi | |
| 2013/0046330 A1 | 2/2013 | McIntosh et al. | |
| 2013/0123835 A1* | 5/2013 | Anderson | A61F 2/00 606/200 |
| 2013/0245669 A1 | 9/2013 | Basu et al. | |
| 2014/0172006 A1 | 6/2014 | Stack et al. | |
| 2014/0180329 A1 | 6/2014 | Krahbichler | |

FOREIGN PATENT DOCUMENTS

| | | |
|---|---|---|
| WO | 2008066881 A1 | 6/2008 |
| WO | 2008073964 A2 | 6/2008 |
| WO | 2013074521 A1 | 5/2013 |
| WO | 2013134194 A1 | 9/2013 |

OTHER PUBLICATIONS

U.S. Appl. No. 13/782,755, filed Mar. 1, 2013.
U.S. Appl. No. 13/782,677, filed Mar. 1, 2013.
U.S. Appl. No. 13/782,657, filed Mar. 1, 2013.

* cited by examiner

EMBOLIC PROTECTION DEVICE

BACKGROUND OF THE INVENTION

The present disclosure generally relates to devices and systems for use within blood vessels, and more particularly to devices and systems for use within blood vessels that deflect and/or trap emboli.

Arterial embolism is a sudden interruption of blood flow to an organ or body part due to an embolus, e.g., debris or a clot. During a medical procedure, thrombi may form and emboli may move, dislodge or break free within arteries. As used herein, the term emboli refers generally to any particles or debris moving within the bloodstream. These emboli are capable of traveling far from their origins, migrating to other sites of the vasculature where they may obstruct the flow of blood. For example, an embolus may travel through the carotid artery and inhibit the flow of blood to the brain, which may result in the death of brain cells, i.e., cause a stroke. Blockage of the carotid arteries is the most common cause of a stroke.

BRIEF SUMMARY OF THE INVENTION

Disclosed herein are embolic protection devices and systems for inhibiting the passage of emboli into at least one artery of a plurality of arteries in a patient, each of the plurality of arteries being connected at an ostium to the aortic arch.

In an embodiment, an embolic protection device for inhibiting the passage of emboli into at least one artery of a plurality of arteries in a patient, each of the plurality of arteries being connected at an ostium to the aortic arch, may include an anchor section positionable within one of the plurality of arteries, and a shield section operatively coupled to the anchor section. The shield section may be deployed within the aortic arch, and the anchor section may facilitate apposition of the shield section with respect to the ostium of the at least one artery.

In another embodiment, an embolic protection device for inhibiting the passage of emboli into at least one artery of a plurality of arteries in a patient, each of the plurality of arteries being connected at an ostium to the aortic arch, may include an anchor section having a conical configuration having a closed end and an open end. The anchor section may be positioned within one of the plurality of arteries. A shield section may be deployed within the aortic arch. An arm member may include a first end that is operatively coupled to the anchor section and a second end that is operatively coupled to the shield section. The arm member may have a first end operatively coupled to the anchor section and a second end that is operatively coupled to the shield section. The arm member may be configured to be bendable and biased toward a substantially J-shaped configuration.

In a still further embodiment, an embolic protection system for inhibiting the passage of emboli into at least one artery of a plurality of arteries in a patient, each of the plurality of arteries being connected at an ostium to the aortic arch, may include an embolic protection device and a delivery catheter having a longitudinally extending lumen. The embolic protection device may be transitionable between a compressed condition and an expanded condition. The embolic protection device may be translated through the lumen when in a compressed condition and translated to an expanded condition when deployed from the delivery catheter. The embolic protection device may include an anchor section and a shield section, which are operatively coupled to one another. The anchor section may be positionable within one of the plurality of arteries, and a shield section operatively coupled to the anchor section. The shield section may be deployed within the aortic arch. The anchor section may facilitate apposition of the shield section with respect to the ostium of the at least one artery.

These and other embodiments of the present disclosure are more fully described below.

BRIEF DESCRIPTION OF THE DRAWINGS

Embodiments of the present disclosure are described with reference to the accompanying drawings, in which.

DETAILED DESCRIPTION

Particular embodiments of the present disclosure are described with reference to the accompanying drawings. In the figures and in the description that follow, like reference numerals identify similar or identical elements. As used throughout the following description, the term "proximal" refers to the end or portion of a device that is relatively close to the user deploying the device, and the term "distal" refers to the end or portion of the device that is relatively farther away from the user deploying the device.

Figure 1:
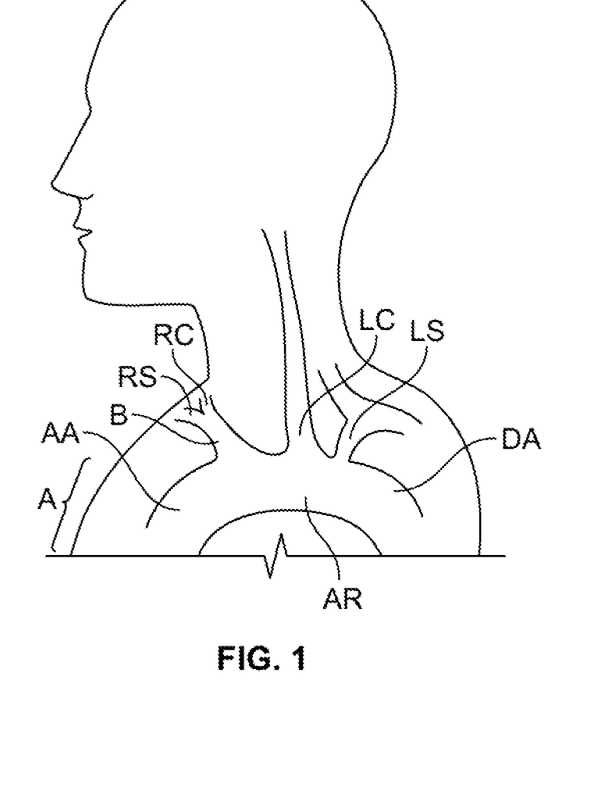
FIG. 1 is a diagrammatic view of a portion of a patient's vasculature system.

The aorta is the main trunk of a series of vessels that convey oxygenated blood to the tissues of the body. As shown in FIG. 1, aorta A includes ascending aorta AA, which commences at the upper part of the left ventricle of the heart. After ascending for a short distance, aorta A arches backward and to the left side to form aortic arch AR, which transitions to descending aorta DA, which descends within the thorax. Aortic arch AR commonly includes three arterial branches: brachiocephalic artery B, left common carotid artery LC, and left subclavian artery LS. Brachiocephalic artery B supplies blood to the right arm, the head, and the neck. Typically, brachiocephalic artery B includes a common brachiocephalic trunk, which branches into right subclavian artery RS and right common carotid artery RC. Left common carotid artery LC branches into internal and external vessels near the top of the thyroid, and supplies blood to the brain and other tissues within the skull. Left subclavian artery LS supplies blood to the left arm, with some branches supplying blood to the head and thorax. It is to be understood that the anatomy of a particular individual may differ, and that the description of particular anatomical features is merely illustrative and should not be construed as limiting the disclosure.

A thrombus or blood clot may form within an artery, when blood flow is sluggish, enabling clotting factors to accumulate and giving platelets an opportunity to stick together. An embolus is most often a piece of a thrombus that has broken free. However, an embolus may also be plaque, fat, calcification, and/or other material. An embolus travels with the flowing blood until it reaches a narrowing in the artery through which it cannot pass, blocking the artery. During a vascular procedure, such as a transcatheter aortic valve implantation (TAVI) procedure (also known as transcatheter aortic valve replacement (TAVR) procedure), emboli may be dislodged as surgical instrumentation passes through the vasculature, and, for example, causes plaque to become dislodged or scrapes tissue from the artery during the translation of the instrumentation.

Various embodiments of devices and systems for deflecting and/or capturing emboli are described with reference to FIGS. 2A-14. One such embodiment of an embolic protection device is shown and described with reference to FIGS. 2A-2D. Embolic protection device 10 includes shield section 12 and anchor section 14. Anchor section 14 may be positioned at an approximate center of shield section 12 such that axis y, which extends longitudinally through anchor section 14, is substantially at the center of shield section 12. Shield section 12 may include wing-like first and second sections 12a, 12b. Anchor section 14 is configured to be frictionally secured within an ostium, i.e., opening, of one of arterial branches B, LC, and LS to anchor the device 10 within aortic arch AR. Anchor section 14 may have a configuration that is generally cylindrical about its longitudinal axis y extending longitudinally therethrough.

Figure 2A:
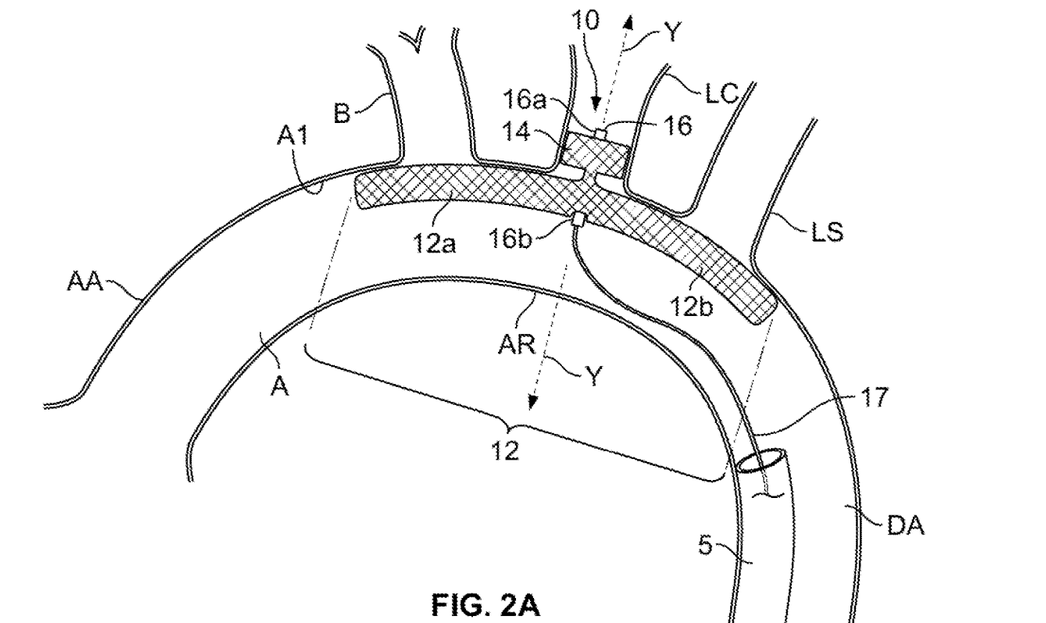
FIG. 2A is a diagrammatic view of an embodiment of an embolic protection device deployed within a patient's vasculature.
Figure 2B:
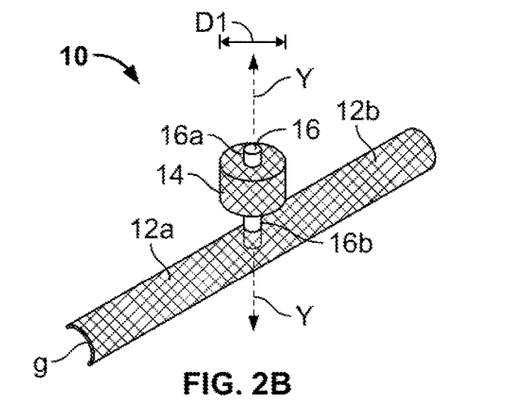
FIG. 2B is a perspective view of the embolic protection device of FIG. 2A.
Figure 2C:
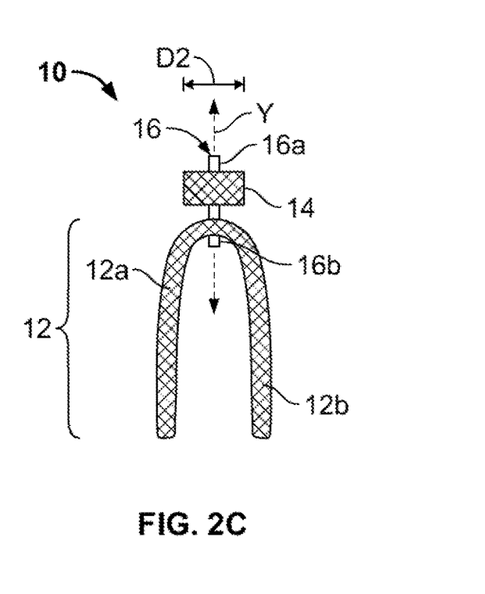
FIG. 2C is a side view of the embolic protection device of FIG. 2A in a second condition.

Shield section 12 and anchor section 14 may be integrally formed (FIG. 2A) or may be formed as separate components that are operatively connected to one another (FIGS. 2B-2C). Connector 16, such as a screw or other fastener, may extend through anchor section 14 and shield section 12 to couple those sections to one another and/or to facilitate the coupling of device 10 to wire 17. Connector 16 may have a first end 16a and a second end 16b. At least one of first end 16a and second end 16b may be coupled to wire 17 to facilitate the delivery of the embolic protection device 10 into the patient's vasculature.

First and second sections 12a and 12b of shield section 12 may be oriented substantially co-linearly in a direction transverse to the axis y, and each may be curved about its own longitudinal axis. In that regard, sections 12a and 12b may have a radius of curvature g (shown in FIG. 2B), which complements or corresponds to the transverse cross-section of aorta A in the region of aortic arch AR to facilitate apposition of the first and second sections against upper surface A1 of aortic arch AR so that the ostia of arterial branches B, LC, and/or LS are shielded by shield 12 without obstructing passage of instrumentation, e.g., instrumentation used during a TAVI procedure, through aortic arch AR.

The exterior surfaces of shield section 12 and anchor section 14 are configured to deflect and/or capture emboli in the blood while allowing blood to continue flowing through arterial branches B, LC, and LS. In that regard, at least the exterior surfaces of shield section 12 and anchor section 14 may be formed from a braided or mesh-like material. The braided or mesh-like material may include a plurality of wires that are woven together so that openings are formed between the wires. The braided or mesh-like material allows blood to flow through the exterior surfaces of shield section and anchor section 14 while deflecting emboli that are larger than a predetermined size. A filter may be disposed within the exterior surfaces formed by the braided or mesh-like material, or may be attached to the braided or mesh-like material, to capture or trap emboli that are small enough to pass through the exterior surfaces of shield section 12 and anchor section 14 as the blood flows therethrough. The filter may be formed from a polymer, such as a polyurethane foam, a sufficiently porous fabric material, or other similar types of materials capable of providing a filtering function.

Device 10 may be formed from a material that is transitionable between an expanded state (FIG. 2B) and a compressed state (FIG. 2C). The material may have shape memory properties, such as exhibited by a nickel titanium alloy, and may be biased toward the expanded state such that, after being compressed, the material will transition back toward the expanded state. As shown in FIG. 2B, in the expanded state of device 10, the anchor section 14 has diameter D1, and first and second sections 12a, 12b of shield section 12 are oriented substantially co-linearly in a direction transverse to axis y. In the compressed state, on the other hand, section 14 has diameter D2 that is smaller than diameter D1, and first and second sections 12a, 12b of shield section 12 are oriented substantially parallel to one another and to axis y.

Device 10 may be deployed within a patient's vasculature using catheter-based techniques to achieve desired placement. The delivery of the device 10 may occur via a transfemoral approach (through the inguinal crease), a transradial approach (through an artery in the arm), or any other percutaneous approach. Device 10 may be compressed and loaded into a delivery catheter in the compressed condition or may come preloaded, and may then be inserted into the patient's vasculature and moved toward aortic arch AR. Device 10 is deployed before the primary procedure, such as the TAVI procedure, and stays in place throughout the procedure to provide embolic protection.

Depending upon which of the percutaneous approaches is followed, either first end 16a or second end 16b of connector 16 may be operatively coupled to wire 17. For example, in a transfemoral approach, in which the delivery catheter is maneuvered up through the aortic arch, anchor section 14 may be positioned at or near the distal end of the delivery catheter with shield section 12 positioned proximally thereof, and second end 16b of connector 16 may be coupled to wire 17. The distal end of the delivery catheter may be maneuvered until it is positioned within the ostium of, for example, the left carotid artery LC. Once the delivery catheter is properly positioned, wire 17 may be distally translated through the delivery catheter to push anchor section 14 out of the delivery catheter and into the ostium of left carotid artery LC. Upon being deployed from the delivery catheter, anchor section 14 will expand to contact and frictionally engage the wall of left carotid artery LC. Subsequently, shield section 12 may be deployed from the delivery catheter by further pushing wire 17 through the delivery catheter. When shield section 12 has been released from the delivery catheter, first and second sections 12a, 12b may expand outwardly until they contact the upper surface A1 of the aortic arch AR, as shown in FIG. 2A.

In this deployed condition, first and second sections 12a and 12b of shield section 12 apply an appositional force against upper surface A1 of aortic arch AR such that first section 12a covers the ostium leading to brachiocephalic artery B, and second section 12b covers the ostium leading to left subclavian artery LS. Both anchor section 14 and shield section 12 cover the ostium leading to left common carotid artery LC. A similar procedure may be used to deploy anchor section 14 of device 10 in either brachiocephalic artery B or left subclavian artery LS.

Figure 2D:
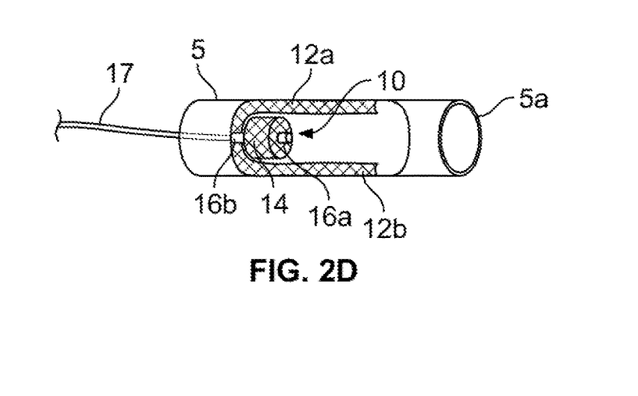
FIG. 2D is a perspective view of the embolic protection device of FIG. 2A retracted into a delivery catheter, with the delivery catheter partially broken away to see the interior thereof.

Once the surgical procedure, such as the TAVI procedure, has been completed, device 10 may be retrieved. For example, wire 17, which may remain attached to device 10, may be drawn back into the delivery catheter. Alternatively, device 10 may be fully released from wire 17 after deployment, and may thereafter be reconnected to wire 17 to recapture device 10 after completion of the desired surgical procedure. When utilizing a transfemoral approach, the shield section 12 may be retrieved back into the delivery catheter first. As shown in FIG. 2D, as first and second sections 12a, 12b contact open distal end 5a of delivery catheter 5, they will be deformed to a compressed state in which they are oriented substantially parallel to one another and positioned distally relative to anchor section 14. That is, first and second sections 12a, 12b will fold on either side of anchor section 14. Continued pulling on wire 17 will cause anchor section 14 to compress as it is drawn together with sections 12a and 12b into delivery catheter 5. During removal of device 10, any captured and/or trapped emboli within shield section 12 and/or anchor section 14 will be removed along with the device.

In an alternative delivery method, device 10 may be delivered to the deployment site using, for example, a left carotid artery or radial approach in which the delivery device is fed into and through one of the arterial branches until it reaches the junction with the aortic arch AR. In such a case, shield section 12 may be positioned at or near the distal end of the delivery catheter (with the fee ends of sections 12a and 12b facing toward the open distal end of the delivery catheter) and with anchor section 14 positioned proximally thereof, and guide wire 17 may be operatively coupled to first end 16a of connector 16. In deploying device 10, once the delivery catheter has been properly positioned at the junction of the left carotid artery LC and the aortic arch AR, guide wire 17 may be pushed distally, forcing shield section 12 out from the delivery catheter. Once released, first section 12a and second section 12b of shield section 12 may expand outwardly and into contact with upper surface A1 of aortic arch AR. Continued pushing on wire 17 will expel anchor section 14 from the delivery catheter, whereupon it will expand into frictional engagement with the wall of left carotid artery LC, thereby holding device 10 in place. When retrieving device 10 following a surgical procedure, the device may be withdrawn into the delivery catheter by pulling on wire 17. As anchor section 14 will be drawn into the catheter before shield section 12, device 10 will be compressed to the configuration shown in FIG. 2C.

Another embodiment of an embolic protection device 20 is described with reference to FIGS. 3A and 3B. Embolic protection device 20 has a first end 21 and a second end 22, and includes a neck section 23 positioned between an anchor section 25 and a shield section 27. Depending upon the desired delivery approach of device 20, either of first end 21 or second end 22 may be operatively coupled to wire 17. Anchor section 25 and shield section 27 may be formed from a braided, mesh-like material that is molded and/or heat set to form the sections of device 20. The braided, mesh-like material is configured to allow blood to flow therethrough while deflecting emboli greater than a predetermined size. Device 20 may be formed from a nickel titanium alloy or other material having shape memory properties, and may be biased toward the expanded state such that, after being compressed, the material will transition back toward the expanded state. A filter may be operatively coupled to or disposed within anchor section 25 and/or shield section 27 to trap or capture smaller sized emboli that are capable of passing through the braided, mesh-like material. The filter may be formed from the same types of materials described above with reference to device 10.

Anchor section 25 may be generally cylindrical and is configured to be frictionally secured within an ostium of an arterial branch. Shield section 27 may be generally flattened and may define a radius of curvature r (FIG. 3B) corresponding to the natural curvature of aortic arch AR to facilitate apposition between shield section 27 and upper surface A1 of aortic arch AR such that when placed therein, shield section 27 is relatively unobstrusive to the passage of instrumentation through the aortic arch. Neck section 23 is a narrowed region disposed between anchor section 25 and shield section 27. Neck section 23 may flare out in a long, relatively flat body so that shield section 27 is flexible and movable relative to anchor section 25 and neck section 23. Neck section 23 may be made from the same braided, mesh-like material as anchor section 25 and shield section 27, and its relatively flat body may be placed in apposition against upper surface A1 of aortic arch AR to capture and/or deflect of emboli while not substantially interfering with the apposition of shield section 27 with respect to the upper surface of the aortic arch. A biasing element 29, such as a length of shape-memory wire, may be disposed on or within neck section 23 to facilitate such apposition of shield section 27 against upper surface A1 by pulling the shield section toward anchor section 25.

Figure 3A:
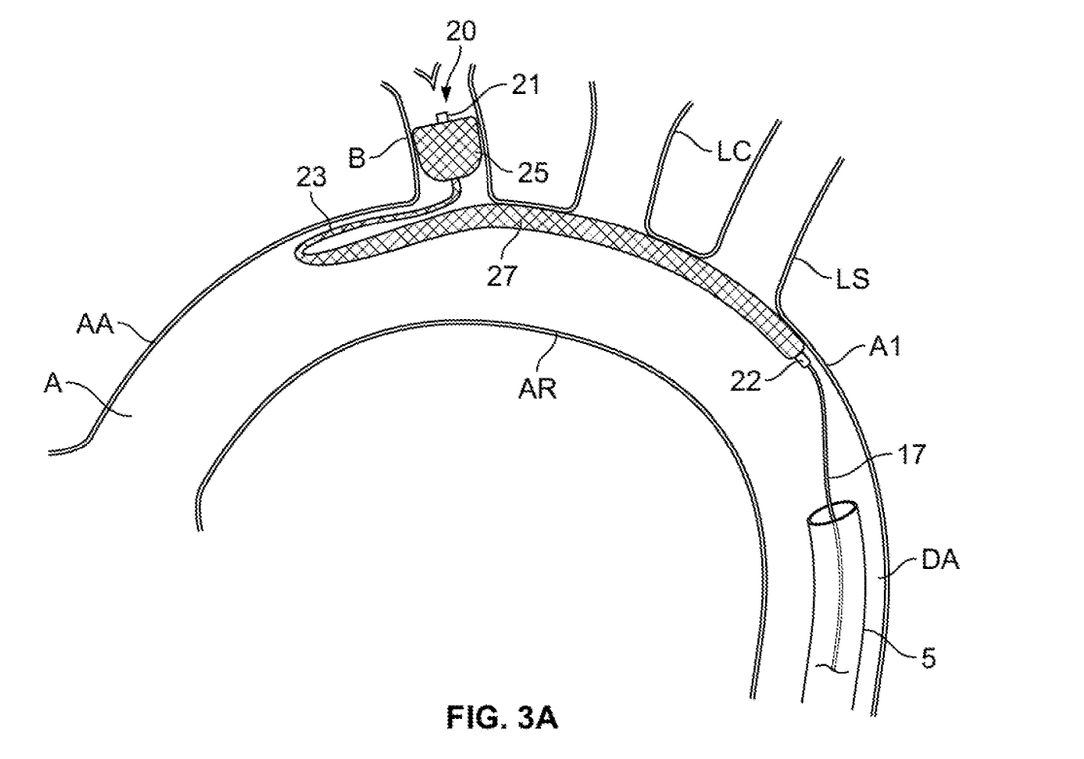
FIG. 3A is a diagrammatic view of another embodiment of an embolic protection device deployed within a patient's vasculature.
Figure 3B:
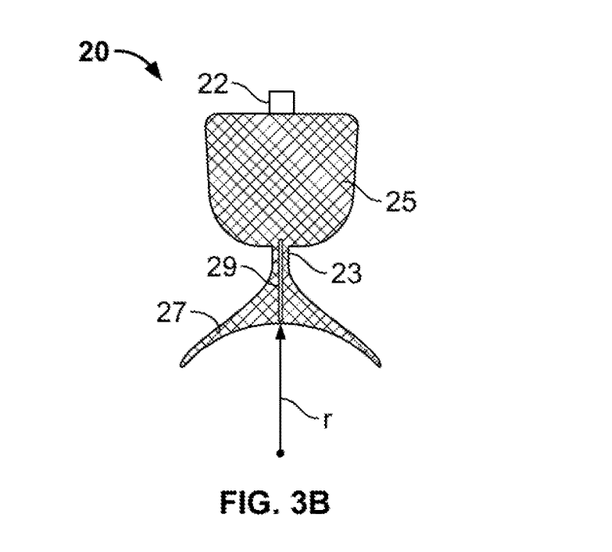
FIG. 3B is an end view of the embolic protection device of FIG. 3A.

As shown in FIG. 3A, when in the deployed condition, anchor section 25 is frictionally secured within brachiocephalic artery B, and neck section 23 biases shield section 27 against upper surface A1 of aortic arch AR so that the shield section overlies one or more ostia leading to the arterial branches B, LC, and/or LS. The biasing element 29 may be configured in a predetermined shape so that shield section 27 is relatively close to anchor section 25. Forming biasing element or wire 29 from a nickel titanium alloy or other material having shape memory properties causes the biasing element to move toward the predetermined shape when deflected away from that shape, such as when device 20 is loaded in a delivery catheter.

Device 20 is deliverable to the deployment site within the patient's vasculature using the same percutaneous approaches as described above with respect to device 10, and may be deployed in substantially the same manner. Device 20 may be compressed and loaded into delivery catheter 5 in the compressed condition. While device 20 is positioned within delivery catheter 5, the delivery catheter may be inserted into the patient's vasculature and moved toward aortic arch AR.

When utilizing a transfemoral approach, as shown in FIG. 3A, wire 17 may be operatively coupled to second end 22 of device 20. As delivery catheter 5 is brought near the ostium leading to brachiocephalic artery B, wire 17 may be distally advanced through the delivery catheter to push anchor section 25 out from the delivery catheter and into the brachiocephalic artery. As anchor section 25 is deployed, it expands to anchor itself within brachiocephalic artery B. Once anchor section 25 has been deployed, neck section 23 and shield section 27 may be deployed in that order by further advancement of wire 17. As neck section 23 and shield section 27 are expelled from delivery catheter 5, biasing member 29 moves back toward its predetermined shape, urging the neck section toward upper surface A1 of aortic arch AR and drawing the shield section in a direction toward the upper surface of the aortic arch such that the shield section covers the ostia leading to arteries B, LC, and LS. After deployment, device 20 may remain attached to wire 17 or may alternatively be fully released from the wire and reconnected to the wire when recapturing and retrieving the device. Device 20 remains in that position during the desired surgical procedure, such as the TAVI procedure, following which its retrieval may be achieved by pulling wire 17 proximally back through delivery catheter 5. It will be appreciated that, as wire 17 is retracted, shield section 27 will be withdrawn into delivery catheter 5 first, followed by neck section 23 and anchor section 25.

Figure 4:
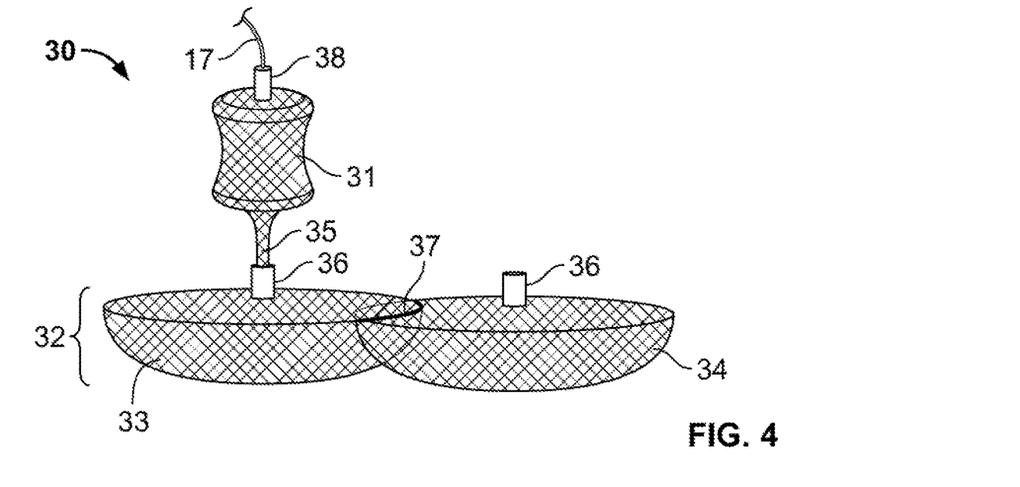
FIG. 4 is a perspective view of still another embodiment of an embolic protection device.
Figure 5A:
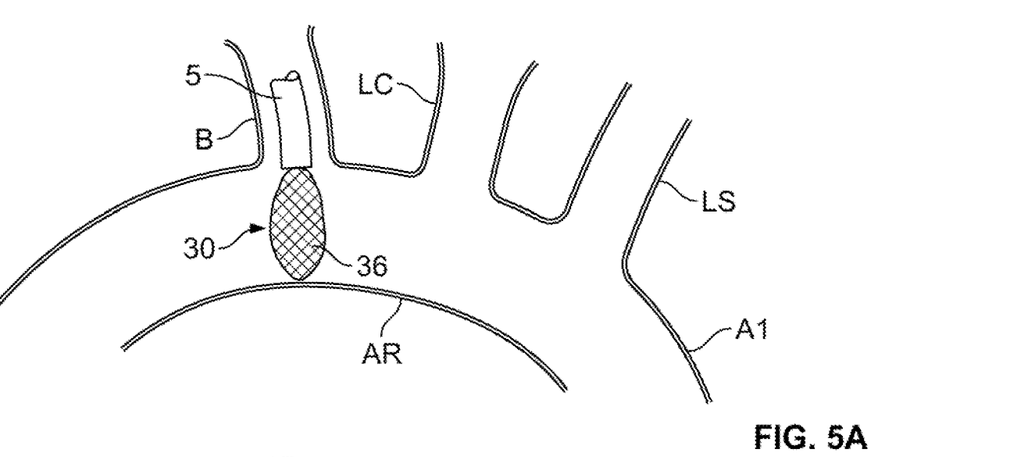
FIG. 5A is a diagrammatic view of the embolic protection device of FIG. 4 partially deployed within a patient's vasculature.
Figure 5B:
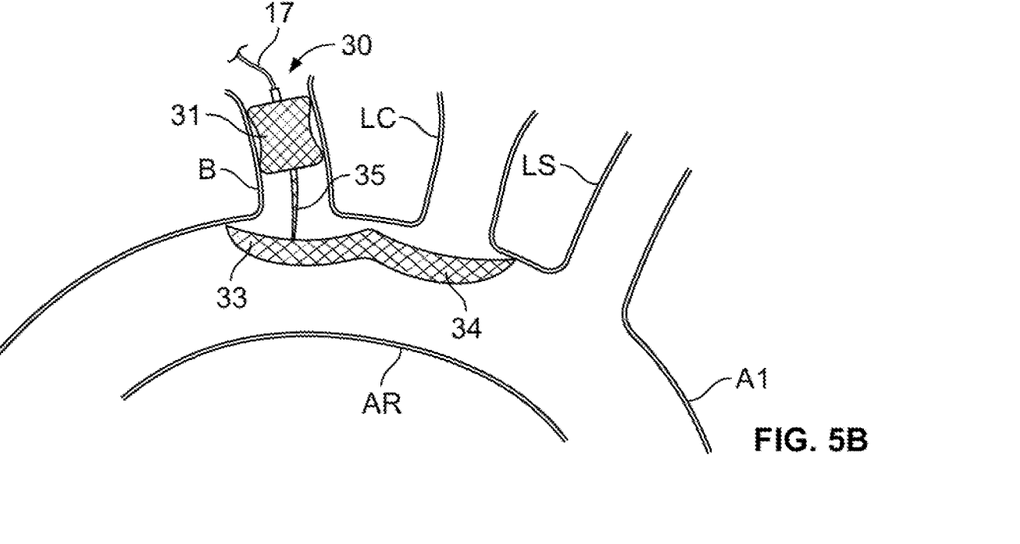
FIG. 5B is a diagrammatic view of the embolic protection device of FIG. 4 fully deployed within a patient's vasculature.

Another embolic protection device 30 is shown in FIGS. 4-5B. Embolic protection device 30 may include anchor section 31 and shield section 32, which may include deflector discs 33 and 34. Anchor section 31 and shield section 32 may be formed from the braided, mesh-like material noted above in connection within the previously described embodiments. Anchor section 31 may be generally cylindrical, and may include an elongated, narrowed neck section 35 projecting from one end thereof toward shield section 32. Neck section 35 may be integrally formed with anchor section 31, and may be operatively coupled to deflector disc 33 of shield section 32 via a crimp tube 36, which may couple a free end of neck section 35 to an end surface of deflector disc 33. One or more crimp tubes 36 may crimp the free ends of the braided, mesh-like material to inhibit unraveling of the material of anchor section 31 and deflector discs 33 and 34. However, heat setting of the braided, mesh-like material may minimize the likelihood of unraveling of the loose ends of the material even if the material are not contained in crimp tubes 36. The transverse cross-section of neck section 35 may be sufficiently narrow that shield section 37 can readily pivot relative to anchor section 32. Another crimp tube 38 may be coupled to the end of anchor section 31 opposite neck section 35 to crimp the braided, mesh-like material therein, and may serve to couple a wire 17 to device 30. It is to be understood that anchor section 31 and shield section 32 may be operatively coupled to one another and/or to wire 17 via any suitable connection means including, for example, a screw.

Deflector discs 33 and 34 may be secured to one another in an overlapping fashion such that a portion of deflector disc 33 overlaps deflector disc 34 and vice versa. Alternatively, deflector discs 33 and 34 may be joined to one another in edge-to-edge fashion along a waist 37, which may follow the contour of deflector disc 33. Discs 33 and 34 may twist relative to one another at waist 37. Deflector discs 33 and 34 may have substantially the same diameter and thickness or one disc may have a larger diameter and/or thickness than the other. Anchor section 31 may extend substantially perpendicularly from the approximate center of deflector disc 33. A porous polymer material may be disposed within each of deflector discs 33 and 34.

As with the previously described embodiments, the device 30 may be compressible to a collapsed condition for insertion into a delivery catheter, and preferably may be formed from a nickel titanium alloy or other shape memory material biased toward the expanded condition so that, upon deployment from the delivery catheter, it will automatically expand. In the expanded and unconstrained condition, deflector discs 33 and 34 will be positioned alongside one another, with deflector disc 33 oriented substantially perpendicular to neck section 35, and neck section 35 oriented substantially coaxially with anchor section 31.

The delivery and deployment of embolic protection device 30 will be described with reference to FIGS. 5A and 5B. Device 30 may be delivered via radial, brachial access from the patient's right arm or via any other suitable percutaneous approach. Device 30 may be delivered to a desired position in the patient's vasculature by placing the device within delivery catheter 5 while in a compressed condition. Deployment of device 30, and subsequent recapture thereof, may be achieved through manipulation of wire 17. When delivered via a transradial approach, delivery catheter 5 may be moved through brachiocephalic artery B until its distal end is positioned in aortic arch AR. At this juncture, wire 17 may be pushed distally through the delivery catheter 5 until the deflector disc 34 is expelled, followed by the deflector disc 33. As they are deployed from delivery catheter 5, deflector discs 33 and 34 will expand and be biased to an orientation substantially perpendicular to neck section 35. That is, with neck section 35 still within delivery catheter 5, deflector discs 33 and 34 will become oriented substantially perpendicular to the longitudinal axis of the delivery catheter. During deployment, deflector disc 34 may twist relative to deflector disc 33. Withdrawing delivery catheter 5 slightly will pull deflector discs 33 and 34 upwardly into contact with upper surface A1 of aortic arch AR, whereupon deflector disc 33 will be positioned over the ostium of brachiocephalic artery B and deflector disc 34 will be positioned over the ostium of left carotid artery LC.

Continued advancement of wire 17 through delivery catheter 5 will push anchor section 31 out of the delivery catheter and into brachiocephalic artery B. Upon being deployed from the delivery catheter, anchor section 31 will radially expand to contact and frictionally engage the wall of the brachiocephalic artery. Tension in neck section 35 will hold shield section 32 against upper surface A1 of aortic arch AR, such that a clinician does not have to manually supply tension to the shield section. In the deployed position of shield section 32, deflector disc 33 is configured to prevent emboli from entering brachiocephalic artery B, and deflector disc 34 is configured to prevent emboli from entering left carotid artery LC. However, the low profile of discs 33 and 34 enables surgical instrumentation for performing a desired surgical procedure to pass through aortic arch AR. After completion of the surgical procedure, retrieval of device 30 is achieved by pulling wire 17 so as to pull anchor section 31, neck section 35, deflector disc 33, and deflector disc 34 back into and through the delivery catheter.

Figure 6A:
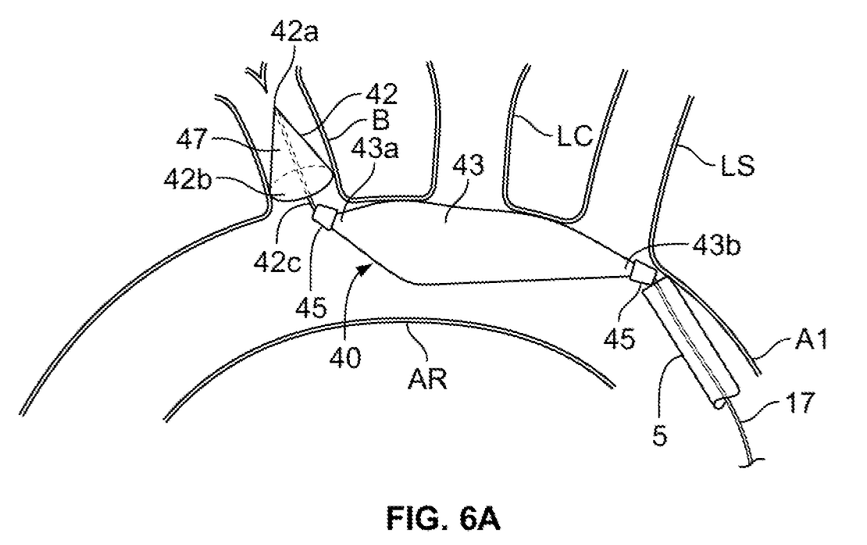
FIG. 6A is a diagrammatic view of another embodiment of an embolic protection device deployed within a patient's vasculature via a first access approach.
Figure 6B:
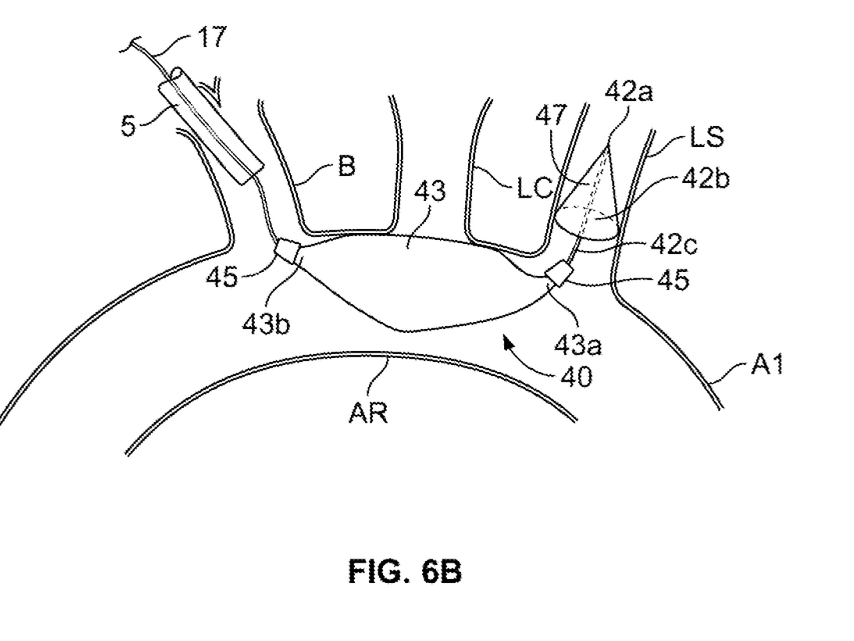
FIG. 6B is a diagrammatic view of the embolic protection device of FIG. 6A deployed within a patient's vasculature via a second access approach.

Yet another embodiment of an embolic protection device 40 is shown in FIGS. 6A-6B. Device 40 includes anchor section 42 and shield section 43. Anchor section 42 may be generally cone shaped, with a pointed closed end 42a and an open end 42b. Shield section 43 may have a first end 43a and a second end 43b, and a low profile, i.e., it may be relatively thin. Anchor section 42 may be coupled to shield section 43 so that its open end 42b is positioned closer to shield section than its closed end 42a. Connecting wire 42c may operatively couple anchor section 42 to shield section 43. Connecting wire 42c may extend from closed end 42a though the interior of anchor section 42 and open end 42b, at which point it may be coupled to first end 43a of shield section 43.

Anchor section 42 and shield section 43 each may be formed from a braided or mesh-like material through which blood may flow while emboli are deflected and/or captured. A filter may be disposed within or attached to the braided or mesh-like material to capture or trap emboli that are small enough to pass through the exterior surfaces of anchor section and the shield section 43. Shield section 43 may be operatively coupled at its second end 43b to wire 17 by crimp tube 45 or by any other suitable attachment means, such as a screw. Ends 43a and 43b of shield section 43 may each be contained within a crimp tube 45 to inhibit unraveling of the free ends of the braided, mesh-like material forming the shield section. Alternatively, or in addition, heat setting of the material forming shield section 43 may inhibit such unraveling of the braided material. The crimping of ends 43a and 43b and/or the heat setting of shield section 43 may cause the shield section to have a tapered configuration that facilitates both its deployment from and recapture into a delivery catheter.

Device 40 may be transitionable between a compressed condition and an expanded condition, and may be biased toward the expanded condition so as to expand as it is deployed from a delivery catheter. Accordingly, device 40 is preferably formed from a nickel titanium alloy or other material having shape memory properties. Pointed closed end 42a of anchor section 42 may be configured to be inserted first into one of the arterial branches so that the tapered, conical shape of the anchor section facilitates insertion of the anchor section into the arterial branch. When positioned within one of the arterial branches, anchor section 42 may transition toward its expanded configuration so as to frictionally engage the arterial branch, thus anchoring itself therein. When deployed within an arterial branch B, LC, or LS, anchor section 42 facilitates positioning of the shield section 43 in front of the opening to the arterial branch to inhibit passage of emboli therethrough. In that regard, anchor section 42 may include a hollow region 47 in which emboli may be captured.

Device 40 may be deployed within a patient's vasculature using catheter-based techniques to achieve a desired placement. Device 40 may be compressed and loaded into a delivery catheter (not shown) in the compressed condition. While device 40 is positioned within the delivery catheter, the delivery catheter may be inserted into the patient's vasculature and moved toward aortic arch AR. This may be accomplished in a number of ways, including a transfemoral approach depicted in FIG. 6A, a transradial approach depicted in FIG. 6B, or any other percutaneous approach. In the transfemoral delivery approach, the delivery catheter may be maneuvered up through aortic arch AR and toward, for example, the brachiocephalic artery B until the distal end of the delivery catheter is positioned through the ostium of the brachiocephalic artery. Anchor section 42 may then be deployed from the delivery catheter and into the brachiocephalic artery B by pushing wire 17 through the delivery catheter. As it is expelled from the delivery catheter, anchor section 42 will radially expand until the large diameter, open end 42b thereof contacts and exerts a radial force against the wall of the brachiocephalic artery to block the ostium leading to same. Once anchor section 42 is secured within the brachiocephalic artery B, shield section 43 may be deployed in aortic arch AR by pushing wire 17 farther through the delivery catheter while simultaneously withdrawing the catheter. It will be appreciated, of course, that anchor section 42 may be deployed either in the left carotid artery LC or the left subclavian artery LS, rather than the brachiocephalic artery B. In such event, however, using the transfemoral approach, shield section 43 will not be able to cover the ostia of the other two arteries, as will be apparent from the discussion below.

Following the deployment of shield section 43 from delivery catheter 5, wire 17 may be pulled slightly to hold second end 43b of shield section 43 against the distal end of the delivery catheter, and the delivery catheter may then be pressed against upper surface A1 of aortic arch AR. This will create tension in shield section 43 and hold it against upper surface A1 of aortic arch AR over the ostia leading to one or more of arterial branches B, LC, and LS.

In the transradial delivery approach, as shown in FIG. 6B, the delivery catheter may be maneuvered through brachiocephalic artery B and into aortic arch AR. The delivery catheter may be further advanced toward left subclavian artery LS until the distal end of the delivery catheter is positioned through the ostium of the left subclavian artery. Anchor section 42 then may be deployed from delivery catheter 5 and into left subclavian artery LS by pushing wire 17 through the delivery catheter. As it is pushed out from delivery catheter 5, anchor section 42 will radially expand until the large diameter, open end 42b thereof contacts and exerts a radial force against the artery wall. Once anchor section 42 is secured within left subclavian artery LS, shield section 43 may be deployed from the delivery catheter by pushing wire 17 farther through the delivery catheter while simultaneously withdrawing the delivery catheter. Using the transradial approach, the delivery catheter may alternatively be advanced through left subclavian artery LS and into aortic arch AR for deployment of anchor section 42 in brachiocephalic artery B.

Following the deployment of shield section 43, wire 17 may be slightly pulled upon to hold the shield section against upper surface A1 of aortic arch AR. Shield section 43 blocks arterial branches B and LC, and anchor section 42 is positioned within left subclavian artery LS (FIG. 6B). Once a desired surgical procedure has been completed, device 40 may be retrieved back into delivery catheter 5 by pulling wire 17 with sufficient force to overcome the frictional engagement between anchor section 42 and the arterial branch B, LC, or LS in which it is placed. Shield section 43 and anchor section 42 will collapse to a compressed state as they are drawn into the delivery catheter.

Figure 7:
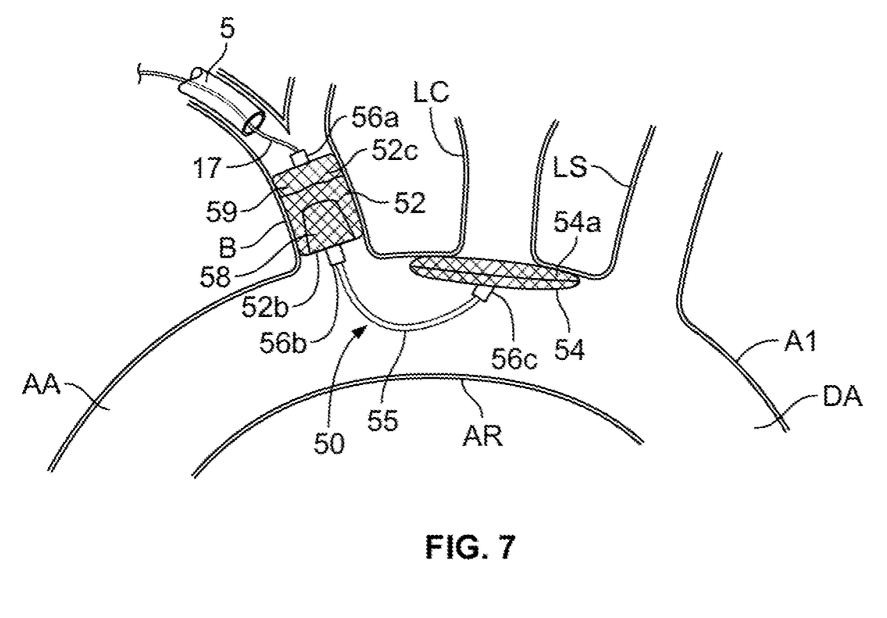
FIG. 7 is a diagrammatic view of another embodiment of an embolic protection device deployed within a patient's vasculature.

A further embolic protection device 50 is shown in FIG. 7. Device 50 includes a generally cylindrical anchor section 52 and a shield section 54 including a deflector disc 54a, all of which may be formed from the same braided, mesh-like material noted above in connection with the previously described embodiments. Device 50 may be coated with an antithrombogenic material, such as heparin. Anchor section 52 may be closed at its distal end 52b and its proximal end 52c, while deflector disc 54 may have a configuration that is generally circular and flattened. The proximal end 52c and the distal end 52b of anchor section 52 and the approximate center of disc 54 may each be captured within a crimp tube 56a-c, respectively. An arm member 55 may be operatively coupled at one end to the distal end 52b of anchor section 52 and at the other end to a flattened surface of deflector disc 54. Arm member 55 may be formed from a material having shape memory properties, such as those exhibited by nickel titanium. The material forming arm member 55 may be braided and/or mesh-like. At the proximal end 52c of anchor section 52, crimp tube 56a may operatively couple the anchor section 52 to a wire 17. The distal end 52b of anchor section 52 may be operatively coupled to arm member 55 by crimp tube 56b. The distal end of arm member 55 may be operatively coupled to disc 54 by crimp tube 56c. Device 50 may be transitionable between an expanded condition and a compressed condition in which the device is compressed to fit within a delivery catheter. In the expanded condition, deflector disc 54 may have a generally ovular or race-track configuration, and may be about the same size as or larger than that of the ostium leading to artery B, LC, and/or LS before which it is to be positioned. Arm member may be biased toward a generally J-shaped configuration such that, when deflected from that configuration, the arm member will push deflector disc 54 upward toward a position adjacent to anchor section 52 so that the deflector disc closes off the ostium leading to the artery before which it is positioned and any blood flowing through that artery will pass through the deflector disc. Device 50 may preferably be formed from a nickel titanium alloy or other shape memory material.

Anchor section 52 may be substantially filled with a filter 58 to facilitate the capture of emboli in the blood passing through the anchor section. In addition, or alternatively, a filter membrane 59, such as a polyurethane sheet, may be disposed within or attached to anchor section 52 adjacent proximal end 52c, and may be configured to capture smaller sized emboli that may pass through the braided mesh-like exterior of the anchor section. Another filter membrane 54a may be disposed within or attached to deflector disc 54, and may be configured to capture smaller sized emboli that may pass through the braided mesh-like exterior of the deflector disc. Filter membrane 54a may have substantially the same diameter as deflector disc 54 while in the expanded condition. Disposing filter membrane 54a may be secured within, e.g., sewn or stitched to an interior surface of, deflector disc 54 to inhibit damage to the filter membrane. Filter 58 and the filter membranes 51 and 59 may be formed from a polymer, such as a polyurethane foam, from a sufficiently porous fabric material, or from other similar types of materials capable of providing a filtering function.

As with the previously described embodiments, device 50 may be compressible to a collapsed condition for insertion into a delivery catheter, and may be biased toward the expanded condition so that, upon deployment from the delivery catheter, it will automatically expand. The delivery of device 50 may occur via a transradial delivery approach or any other percutaneous delivery approach. When delivered via a transradial delivery approach, device 50 may be loaded within delivery catheter 5 so that deflector disc 54 is positioned closer to the open end of the delivery catheter and anchor section 52 is proximal thereof. Delivery catheter 5 may be inserted into the patient's vasculature and moved toward aortic arch AR by way of brachiocephalic artery B. With the distal end of delivery catheter 5 positioned in the brachiocephalic artery B adjacent to the ostium leading to aortic arch AR, device 50 may be deployed from the delivery catheter by pushing wire 17 therethrough. As wire 17 is pushed through delivery catheter 5, deflector disc 54 may be deployed from the delivery catheter and into aortic arch AR, followed by arm member 55. As it is being deployed from delivery catheter 5, arm member 55 may transition toward its generally J-shaped configuration, moving deflector disc 54 toward the ostium of left carotid artery LC and/or left subclavian artery LS. After arm member 55 has been deployed from delivery catheter 5, the delivery catheter may be withdrawn slightly and anchor section 52 may be deployed therefrom into brachiocephalic artery B. Upon deployment from delivery catheter 5, anchor section 52 will radially expand to contact and frictionally engage the wall of brachiocephalic artery B. With device 50 fully deployed, arm member 55 biases deflector disc 54 against the ostium to left carotid artery LC to inhibit the passage of emboli therein. At the same time, anchor section 52 not only holds device 50 in place, but also inhibits the passage of emboli into brachiocephalic artery B. After a desired surgical procedure has been performed, retrieval of device 50 may be achieved by withdrawing or pulling wire 17 back through delivery catheter 5.

Other delivery approaches besides a transradial delivery approach may be used to deliver device 50 including, for example, a left subclavian artery approach or a transfemoral approach. When utilizing such delivery approaches, device 50 may be loaded within delivery catheter 5 with anchor section 52 closer to the open distal end of the delivery catheter and deflector disc 54 positioned proximal thereof. Wire 17 may be operatively coupled via any suitable connection means to disc 54. Delivery catheter 5, when delivery is via a left subclavian artery approach or a transfemoral approach, may be maneuvered so that its distal end is in or adjacent to brachiocephalic artery B, and wire 17 may be pushed through the delivery catheter to push anchor section 52 into the brachiocephalic artery so that it can expand and anchor itself therein. Continued pushing of wire 17 and movement of delivery catheter 5 in a proximal direction deploys the remainder of device 50 so that arm member 55 may bias deflector disc 54 against the ostium to left carotid artery LC. After a desired surgical procedure has been performed, retrieval of device 50 may be achieved by withdrawing or pulling wire 17 back through delivery catheter 5.

Figure 8:
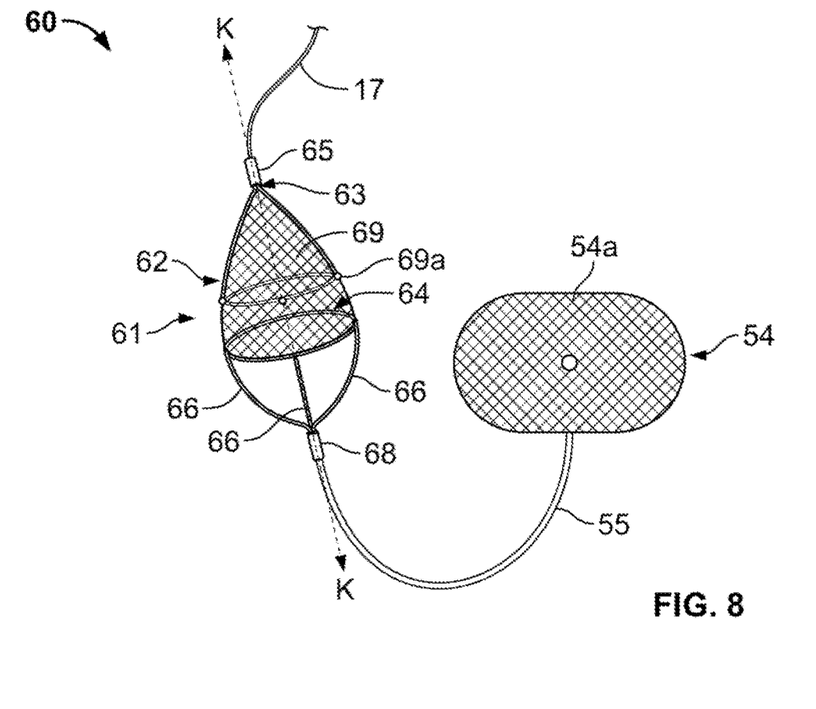
FIG. 8 is a perspective view of a still further embodiment of an embolic protection device.

A still further embodiment of an embolic protection device 60 is shown in FIG. 8. Device 60 includes each of the features of device 50 except as indicated otherwise. In particular, instead of having anchor section 52, device 60 includes an anchor section 61. Anchor section 61 may include a basket 62 that is transitionable between an expanded configuration and a collapsed configuration. In the expanded configuration, basket 62 may have a generally conical configuration with a closed proximal end 63 and an open distal end 64 that may be generally circular. In the collapsed configuration, basket 62 may radially collapse toward axis K, which extends longitudinally through the center of basket 62.

Basket 62 may be formed from a material having shape memory properties, such as those exhibited by a nickel titanium alloy. The material forming basket 62 may be braided and mesh-like. Any loose ends of the braided material may be captured within a crimp tube 65 to inhibit unraveling of the material. Unraveling of the braided, mesh-like material also may be inhibited by heat setting the material. Crimp tube 65 may operatively couple device 60 to a wire 17, which may facilitate deployment and/or retrieval of the device. One or more wires 66 may operatively couple basket 62 of anchor section 61 to arm member 55. In particular, as shown in FIG. 8, three generally equally spaced wires 66 may be secured along a surface of basket 62 and may have their ends captured within a crimp tube 68, which is operatively connected to arm member 55. As discussed above in connection with device 50, arm member 55 is operatively coupled to deflector disc 54. A filter 69 may line a surface of basket 62, preferably the interior surface of basket 62 to protect filter 69 from damage during deployment and/or retrieval of device 60. Stitching 69a may secure filter 69 to basket 62. Filter 69 may facilitate the capture of emboli within blood that may flow through basket 62. Filter 69 may be formed from a polymer, such as a polyurethane sheet, from sufficiently porous fabric material, or from other similar types of materials capable of providing a filtering function. An antithrombogenic coating, such as heparin, may be applied to filter 69 to minimize clotting and the formation of thrombi.

Device 60 may be delivered in substantially the same manner as described with respect to device 50. As with the delivery of device 50, the delivery of device 60 may occur via a transradial delivery approach or any other percutaneous delivery approach, including a transfemoral delivery approach or a left subclavian artery approach. When deployed, anchor section 61 may be positioned within an arterial branch of aortic arch AR, such as brachiocephalic artery B, substantially as described with respect to anchor section 52 of device 50. Once anchor section 61 is anchored within one of the arterial branches, such as brachiocephalic artery B, the remainder of device 60 may be deployed substantially as described with respect to device 50.

Figure 9:
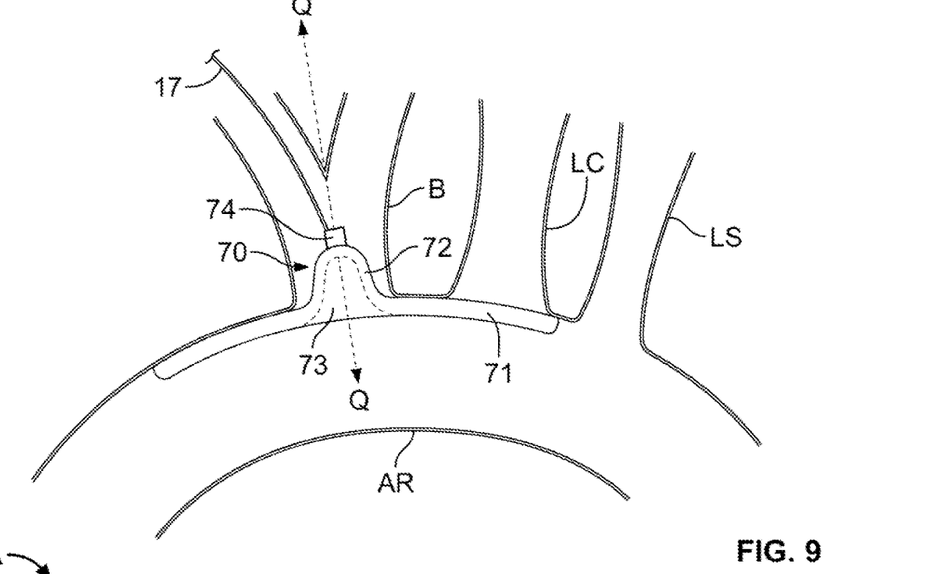
FIG. 9 is a diagrammatic view of another embodiment of an embolic protection device deployed within a patient's vasculature.

Embolic protection device 70 in accordance with another embodiment is shown in FIG. 9. Embolic protection device 70 includes a flanged section 71 and a plug 72 that may be formed integrally with one another. Plug 72 may extend in a proximal direction and in a substantially perpendicular orientation from the approximate center of flanged section 71. In an expanded condition of device 70, flanged section 71 may extend radially outward from the distal end of plug 72. A cup shaped opening 73 may be formed through flanged section 71 and into plug 72 from the distal end thereof. Embolic protection device 70 may be formed from a material having shape memory properties, such as exhibited by a nickel titanium alloy, from a porous foam, or from another compressible material through which blood may flow while inhibiting the passage of emboli. A crimp tube 74 may operatively couple plug 72 to wire 17 to facilitate deployment and/or recapture of embolic protection device 70 using a delivery catheter.

Device 70 may be deployed within a patient's vasculature using catheter-based techniques to achieve desired placement. The delivery of device 70 may occur via a transfemoral approach, a transradial approach, or any other percutaneous approach. Device 70 may be compressed and loaded into a delivery catheter in the compressed condition. While device 70 is positioned within the delivery catheter, the delivery catheter may be inserted into the patient's vasculature and moved toward a desired position at which it is to be deployed. Once the delivery catheter has been properly positioned, wire 17 may be distally translated through the catheter to cause the deployment of device 70. When the delivery catheter approaches aortic arch AR through brachiocephalic artery B, flanged section 71 may be deployed from the delivery catheter and expand first, followed by plug 72, which may expand into anchoring engagement within the artery. Once device 70 is fully deployed and expanded, plug is anchored within brachiocephalic artery B and flanged section 71 covers the opening to left carotid artery LC. Flanged section 71 may have an ovaloid configuration, which may be generally symmetrical with respect to an axis Q extending longitudinally through plug 72, and/or may extend more in one direction than another to cover one or more ostia of the arterial branches near the one in which plug 72 resides. Following completion of the surgical procedure to be performed, device 70 may be retrieved by proximally withdrawing wire 17 through the delivery catheter.

Embolic protection devices 80A, 80B, 90 and 100, described hereinafter, are insertable within one arterial branch B, LC, or LS to provide embolic protection to that arterial branch. It is to be understood that each of devices 80A, 80B, 90 and 100 may be combined with the previously described embolic protection devices that include both anchor sections and shield sections, namely, devices 10-60. In particular, devices 80A, 80B, 90 and 100 may replace the anchor sections 14, 25, 31, 42, 52, and 61 of devices 10-60, respectively, to provide the described anchoring and/or filtering function and may be operatively coupled to the shield sections of each of those devices.

Figure 10:
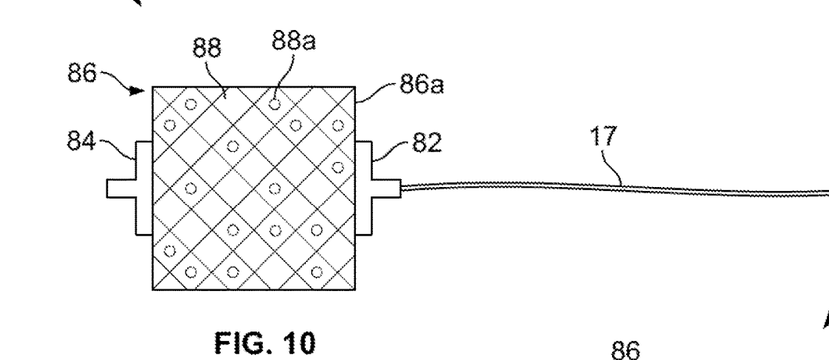
FIG. 10 is a side view of yet another embodiment of an embolic protection device.
Figure 11:
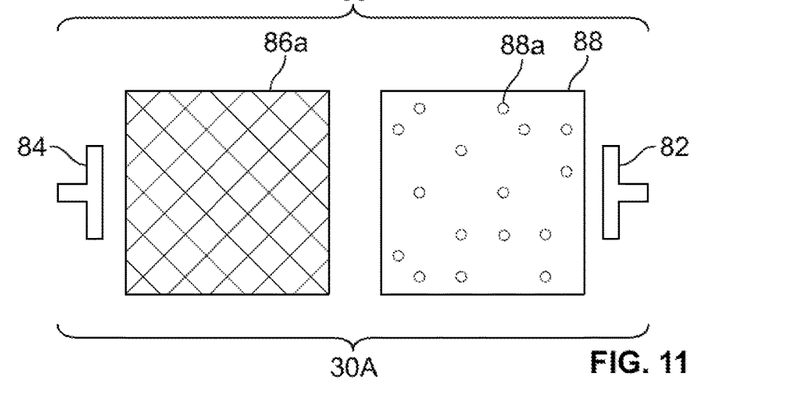
FIG. 11 is an exploded view of the embolic protection device of FIG. 10.

Embolic protection device 80A is described with reference to FIGS. 10-11. Embolic protection device 80A has a hollow, generally cylindrical housing 86 having an outer surface 86a that is configured to permit blood to flow therethrough while deflecting emboli of greater than a predetermined size. A filter 88 formed from a filter material that is configured to allow blood to flow through while capturing smaller sized emboli that may pass through outer surface 86a may substantially fill housing 86. Filter 88 may be formed from the same types of material previously described above in connection with devices 10-60. As shown in FIGS. 10-11, filter 88 may include pores 88a that facilitate the passage of blood therethrough and the capture of emboli therein. Device 80A may be compressible to facilitate delivery via a delivery catheter and may be biased toward an expanded condition to facilitate anchoring of the device within one of the arterial branches B, LC, and LS.

One or more screws 82, 84 may be positioned at each end of housing 86, each of which may operatively couple wire to the housing. Wire 17 may be used to facilitate deployment of device 80A. That is, device 80A may be loaded in a compressed condition in the distal end of a delivery catheter, and wire 17 may be used to translate the device relative to the delivery catheter.

Once the delivery catheter has been positioned at or near the desired location in the patient's vasculature, device 80A may be deployed. For example, device 80A may be deployed in the ostium of one of the arterial branches within the aortic arch, such as the left carotid artery LC. As device 80A is deployed within the arterial branch, the device expands and frictionally engages the arterial branch to anchor it therein. Once the subsequent surgical procedure has been completed, device 80A may be retrieved by proximally translating wire 17 to pull the device back into the delivery catheter. As device 80A is withdrawn into the delivery catheter, it is forced into the compressed condition.

Figure 12:
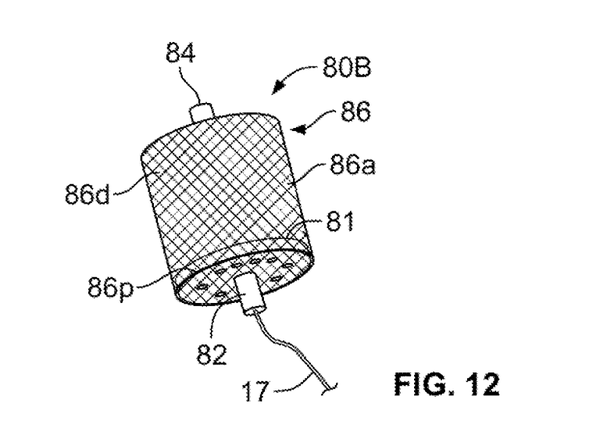
FIG. 12 is perspective view of a still further embodiment of an embolic protection device.

Another embodiment of an embolic protection device 80B is shown and described with reference to FIG. 12. Embolic protection device 80B is substantially similar to device 80A except for the following differences. Instead of having a filter material that substantially fills the space within housing 86, a filter 81 may be operatively coupled to one or both of base 86p or crown 86d of housing 86. Filter 81 may be substantially disc shaped, and may be formed from a polymer, such as a polyurethane foam, from a sufficiently porous fabric material, or from other similar types of materials capable of providing a filtering function. Filter 81 may be disposed within housing 86 to protect the filter material from damage. Deployment and retrieval of device 80B is substantially similar to that of device 80A described above.

Figures 13, 14:
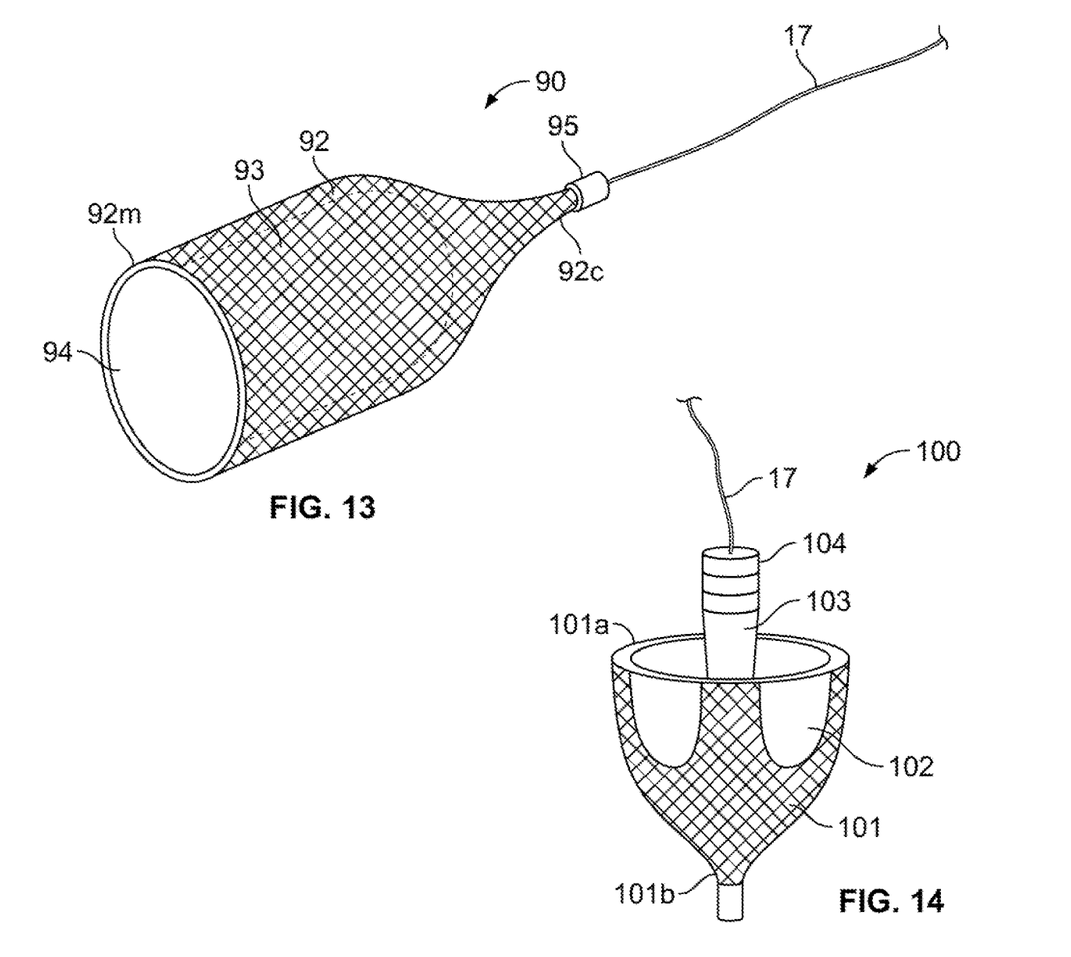
FIG. 13 is a perspective view of yet another embodiment of an embolic protection device.
FIG. 14 is a perspective view of another embodiment of an embolic protection device.

Another embodiment of embolic protection device 90 is shown in FIG. 13. Embolic protection device 90 includes a cup 92 formed from a braided, mesh-like material having shape memory properties, such as a nickel titanium alloy. Cup 92 has an open end 92*m*, tapers to a closed end 92*c*, and has a hollow interior 93. A filter 94 may have a disc-shaped configuration, and may cover or otherwise occlude the open end 92*m*. Filter 94 may be formed from a polymer, such as a polyurethane foam, or from a sufficiently porous fabric material, a perforated polyurethane, or other similar types of materials capable of providing a filtering function so as to permit the flow of blood through cup 92 while capturing emboli that are sufficiently small to pass through the braided material forming the cup.

A crimp tube 95 at closed end 92*c* of cup 92 may be used to couple the cup to wire 17. Crimp tube 95 may crimp the loose ends of the braided, mesh-like material forming cup to inhibit unraveling of the material. Device 90 is positionable within one of arterial branches B, LC, or LS to inhibit passage of emboli therethrough. Emboli less than a predetermined size may pass through openings in the braided material forming cup 92, but may be captured or trapped by filter 94.

Device 90 may be delivered to a desired position in a patient's vasculature by placing the device within a delivery catheter while in a compressed condition. Deployment of device 90, and subsequent recapture thereof, may be achieved through manipulation of wire 17 as described more fully above in connection with the deployment and recapture of the other embodiments of the embolic protection device. The tapered shape of cup 92 may facilitate loading of device 90 into the delivery catheter, as well as recapture of the device for removal from the patient. Device 90 may be deployed within a patient's vasculature using catheter-based techniques substantially as described above with reference to devices 80A and 80B.

FIG. 14 shows another embodiment of an embolic protection device 100. Device 100 has a tapered body 101 with an open end 101*a*, a closed end 101*b*, and a hollow interior 102. Tapered body 101 facilitates translation of embolic protection device 100 through a delivery catheter, insertion and anchoring of the body within an ostium leading to an artery, as well as recapture following a surgical procedure. Hollow interior 102 of tapered body 101 facilitates the capture of emboli within device 100. Hollow interior 102 may have a half-spherical or bowl shape, with a stem 103 extending from the center or low point of the bowl. Stem 103 is attached at one end to closed end 101*b* of tapered body 101 and extends longitudinally therefrom toward a free end that protrudes beyond open end 101*a* of the tapered body. The cross-section of stem 103 may taper downwardly in size from its attachment to tapered body 101 toward its free end.

Device 100 may be formed from a compressible material, such as a material having shape memory properties, including those exhibited by a nickel titanium alloy, from a porous foam, or from another compressible material through which blood may flow while inhibiting passage of emboli. Device 100 may be formed from the braided, mesh-like material noted above in connection with the previously described embodiments. A filter material may be incorporated in hollow interior 102 to facilitate the capture of smaller sized emboli. A crimp tube 104 may be coupled to the free end of stem 103. Crimp tube 104 may crimp the free ends of the braided, mesh-like material of device 100 so as to inhibit the unraveling of the material. Alternatively, or in addition, heat setting the braided, mesh-like material of device 100 may minimize the potential for unraveling. Wire 17 may be coupled to crimp tube 104 to facilitate the deployment of device 100 from or the retrieval of the device into a delivery catheter.

Prior to a surgical procedure, the device 100 may be delivered and deployed in substantially the same manner and using the same approaches as described with reference to device 70. In particular, device 100 may be deployed within a patient's vasculature using any percutaneous catheter-based technique to achieve the desired placement. In particular, device 100 may be delivered to a desired position in a patient's vasculature by placing the device within a delivery catheter while in a compressed condition. Deployment of the device 100, and subsequent recapture thereof, may be achieved through manipulation of wire 17 as described more fully above in connection with the deployment and recapture of the other embodiments of the embolic protection device.

Depending upon the desired delivery approach, wire 17 may be coupled to crimp tube 104 or to closed end 101*b*. In certain procedures, after deployment, open end 101*a* of device 100 may face toward aortic arch AR. In other procedures, after deployment, open end 101*a* of device 100 may face away from aortic arch AR. When open end 101*a* of device 100 faces toward aortic arch AR, emboli may be captured or trapped in filter material within hollow interior 102. When open end 101*a* of device 100 faces away from aortic arch AR, emboli may flow into body 101 and filter material incorporated in hollow interior 102 may inhibit passage of smaller sized emboli.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. It will also be appreciated that the various dependent claims and the features set forth therein can be combined in different ways than presented in the initial claims. It will also be appreciated that the features described in connection with individual embodiments may be shared with others of the described embodiments.

It will be appreciated that the various dependent claims and the features set forth therein can be combined in different ways than presented in the initial claims. It will also be appreciated that any individual features described in connection with any embodiment may be shared with others of the described embodiments. The alternative embodiments presented hereinabove are not mutually exclusive, but may be implemented in various combinations to achieve unique advantages. As these and other variations and combinations of the features discussed above can be utilized without departing from the invention as defined by the claims, the foregoing description of the embodiments should be taken by way of illustration rather than by way of limitation.

By way of illustration only, the embolic protection devices described herein may include an anchor section positionable within one of a plurality of arties; and a shield section operatively coupled to the anchor section, the shield section being deployable within the aortic arch, the anchor section facilitating apposition of the shield section with respect to the ostium of the at least one artery; and/or the anchor section and the shield section may be operatively coupled to a wire; and/or an arm member may operatively couple the anchor section to the shield section; and/or the anchor section and the shield section may each be formed from a braided material; and/or at least one of the anchor section and the shield section may be formed from a shape memory material; and/or at least one of the anchor section and the shield section may include a filter; and/or the filter includes an antithrombogenic coating; and/or the filter may be formed from a porous polymer; and/or the filter may be formed from a porous sheet material; and/or at least one of the anchor section and the shield section may include an opening leading to a hollow interior.

The embolic protection devices may further include an anchor section having a conical configuration with a closed end and an open end, the anchor section being positionable within one of the plurality of arteries, a shield section deployable within the aortic arch, and an arm member having a first end operatively coupled to the anchor section and a second end operatively coupled to the shield section, the arm member being configured to be bendable and biased toward a substantially J-shaped configuration; and/or a filter may line an interior surface of the anchor section; and/or the filter may have an antithrombogenic coating; and/or the anchor section may have an axis extending longitudinally therethrough, and the anchor section may be radially collapsible with respect to the axis; and/or a wire may be operatively coupled to a proximal end of the anchor section; and/or the anchor section may have a cylindrical configuration; and/or the shield section and the anchor section may be formed from a material having shape memory properties.

An embolic protection system as described herein may include an embolic protection device transitionable between a compressed condition and an expanded condition, the embolic protection device including an anchor section positionable within one of the plurality of arteries, and a shield section operatively coupled to the anchor section and being deployable within the aortic arch, the anchor section facilitating apposition of the shield section with respect to the ostium of the at least one artery; and/or a delivery catheter having a longitudinally extending lumen, the embolic protection device being translatable through the lumen when in the compressed condition and transitioning to the expanded condition when deployed from the delivery catheter; and/or a wire operatively coupled to one of the anchor section and the shield section.

The invention claimed is:

1. An embolic protection device for inhibiting the passage of emboli into at least one artery of a plurality of arteries in a human patient, each of the plurality of arteries being connected at an ostium to the aortic arch, the device comprising:
  an anchor section having a compressed state and being biased to an expanded state, the anchor section being positionable within one of the arteries so that, in the expanded state, the anchor section circumscribes and frictionally engages the wall of the one artery at a position spaced from the aortic arch, the anchor section being formed from a first material having a plurality of openings sized to permit the passage of blood through the one artery, but to prevent the passage of emboli larger than a predetermined size through the one artery;
  a shield section having a compressed state and being biased to an expanded state, the shield section in the expanded state having a longitudinal axis and being curved (i) away from the anchor section in a first direction about the longitudinal axis so that the shield section corresponds to the transverse cross-section of the aortic arch and (ii) away from the anchor section in a second direction about an axis orthogonal to the longitudinal axis so that the shield section in the expanded state forms a convex surface facing the anchor section that corresponds to the longitudinal cross-section of the aortic arch to facilitate apposition of the shield section against the upper surface of the aortic arch, the shield section being formed from a second material having a plurality of openings sized to permit the passage of blood from the aortic arch into another one of the arteries, but to prevent the passage of emboli larger than a defined size from the aortic arch into the another artery, the shield section being positionable within the aortic arch in the expanded state so that the plurality of openings of the shield section lie against the ostium of the another artery but not within the another artery when the anchor section is positioned within the one artery and so that the shield section does not circumscribe the circumference of the aortic arch; and
  a connector operatively connecting the shield section to the anchor section at a spaced distance from the anchor section.

2. The embolic protection device of claim 1, wherein one of the anchor section and the shield section is operatively coupled to a wire.

3. The embolic protection device of claim 1, wherein the connector includes an arm operatively coupling the anchor section to the shield section.

4. The embolic protection device of claim 1, wherein the anchor section and the shield section are each formed from a braided material.

5. The embolic protection device of claim 1, wherein at least one of the anchor section and the shield section is formed from a shape memory material.

6. The embolic protection device of claim 1, wherein at least one of the anchor section and the shield section includes a filter separate from the plurality of openings, the filter being formed from a material different from the first material and the second material.

7. The embolic protection device of claim 6, wherein the filter includes an anti-thrombogenic coating.

8. The embolic protection device of claim 6, wherein the filter is formed from a porous polymer.

9. The embolic protection device of claim 6, wherein the filter is formed from a porous sheet material.

10. The embolic protection device of claim 1, wherein the anchor section has a hollow interior.

11. An embolic protection device for inhibiting the passage of emboli into at least one artery of a plurality of arteries in a human patient, each of the plurality of arteries being connected at an ostium to the aortic arch, the device comprising:
  an anchor section having a compressed state and being biased to an expanded state, the anchor section being positionable within one of the arteries so that, in the expanded state, the anchor section circumscribes and frictionally engages the wall of the one artery at a position spaced from the aortic arch, the anchor section being formed from a first material having a plurality of openings sized to permit the passage of blood through the one artery, but to prevent the passage of emboli larger than a predetermined size through the one artery;

a shield section having a compressed state and being biased to an expanded state, the shield section in the expanded state having a longitudinal axis and being curved (i) away from the anchor section in a first direction about the longitudinal axis so that the shield section corresponds to the transverse cross-section of the aortic arch and (ii) away from the anchor section in a second direction about an axis orthogonal to the longitudinal axis so that the shield section in the expanded state forms a convex surface facing the anchor section that corresponds to the longitudinal cross-section of the aortic arch to facilitate apposition of the shield section against the upper surface of the aortic arch, the shield section being formed from a second material having a plurality of openings sized to permit the passage of blood from the aortic arch into another one of the arteries, but to prevent the passage of emboli larger than a defined size from the aortic arch into the another artery, the shield section being positionable within the aortic arch in the expanded state so that the plurality of openings of the shield section lie against the ostium of the another artery but not within the another artery when the anchor section is positioned within the one artery and so that the shield section does not circumscribe the circumference of the aortic arch;

at least one of the anchor section and the shield section including a filter, the filter being formed from a material different from the first material and the second material; and an arm having a first end operatively coupled to the anchor section and a second end operatively coupled to the shield section, the arm being configured to be bendable and biased toward a substantially J-shaped configuration.

12. The embolic protection device of claim 11, wherein the filter lines an interior surface of the anchor section.

13. The embolic protection device of claim 11, wherein the filter has an anti-thrombogenic coating.

14. The embolic protection device of claim 11, wherein the anchor section has an axis extending longitudinally therethrough, and the anchor section is radially collapsible with respect to the axis.

15. The embolic protection device of claim 11, further comprising a wire that is operatively coupled to a proximal end of the anchor section.

16. The embolic protection device of claim 15, wherein the wire is releasably secured to the proximal end of the anchor section.

17. The embolic protection device of claim 11, wherein the anchor section has a cylindrical configuration in the expanded state.

18. The embolic protection device of claim 11, wherein the shield section and the anchor section are formed from a material having shape memory properties.

19. The embolic protection device of claim 11, wherein the anchor section in the expanded state has a conical configuration with a closed end and an open end.

20. An embolic protection system for inhibiting the passage of emboli into at least one artery of a plurality of arteries in a human patient, each of the plurality of arteries being connected at an ostium to the aortic arch, the system comprising:

an embolic protection device having a compressed condition and being biased to an expanded condition, the embolic protection device including:

an anchor section positionable within one of the arteries so that, in the expanded condition, the anchor section circumscribes and frictionally engages the wall of the one artery at a position spaced from the aortic arch, the anchor section having a plurality of openings sized to permit the passage of blood through the one artery, but to prevent the passage of emboli larger than a predetermined size through the one artery;

a shield section having a plurality of openings sized to permit the passage of blood from the aortic arch into another one of the arteries, but to prevent the passage of emboli larger than a defined size from the aortic arch into the another artery, the shield section in the expanded condition having a longitudinal axis and being curved (i) away from the anchor section in a first direction about the longitudinal axis so that the shield section corresponds to the transverse cross-section of the aortic arch and (ii) away from the anchor section in a second direction about an axis orthogonal to the longitudinal axis so that the shield section in the expanded condition forms a convex surface facing the anchor section that corresponds to the longitudinal cross-section of the aortic arch to facilitate apposition of the shield section against the upper surface of the aortic arch, the shield section being positionable within the aortic arch in the expanded condition so that the plurality of openings of the shield section lie against the ostium of the another artery but not within the another artery when the anchor section is positioned within the one artery and so that the shield section does not circumscribe the circumference of the aortic arch; and a connector operatively connecting the shield section to the anchor section at a spaced distance from the anchor section; and a delivery catheter having a longitudinally extending lumen, the embolic protection device being translatable through the lumen when in the compressed condition and transitioning to the expanded condition when deployed from the delivery catheter.

21. The embolic protection device of claim 20, further comprising a wire operatively coupled to one of the anchor section and the shield section.

* * * * *